United States Patent [19]

Nakano et al.

[11] Patent Number: 5,739,024
[45] Date of Patent: Apr. 14, 1998

[54] MALTOHEXAOSE AND MALTOHEPTAOSE-FORMING AMYLASE, AND ITS PREPARATION AND USES

[75] Inventors: Masayuki Nakano; Hiroto Chaen; Toshiyuki Sugimoto; Toshio Miyake, all of Okayama, Japan

[73] Assignee: Kabushiki Kaisha Hayashibara Seibutsu Kagaku Kenkyujo, Okayama, Japan

[21] Appl. No.: 526,082

[22] Filed: Sep. 11, 1995

Related U.S. Application Data

[62] Division of Ser. No. 396,746, Mar. 1, 1995, Pat. No. 5,527,699.

[30] Foreign Application Priority Data

Mar. 1, 1994 [JP] Japan ................................. 6-54371

[51] Int. Cl.⁶ .................... C12N 9/26; C12N 9/28; C12N 1/12; C12N 1/00
[52] U.S. Cl. .................... 435/201; 435/99; 435/202; 435/829; 435/252.1
[58] Field of Search .................... 435/99, 201, 202, 435/829, 252.1

[56] References Cited

FOREIGN PATENT DOCUMENTS 0210597 7/1992 Japan.
0038265 2/1993 Japan.

OTHER PUBLICATIONS

ATCC Catalogue of Bacteria and Bacteriophages, 17th Ed., 1989, pp. 13, 14.
Keiji Kainuma et al, *Isolation and Action Pattern of Maltohexaose Producing Amylase From Aerobacter Aerogenes*, FEBS Letter, vol. 26, pp. 281–285, Oct. 1972.
J. F. Kennedy et al, *Action Pattern and Substrate Specificity of alpha–Amylase K, a Novel Amylase from a Strain of Bacillus Subtilis*, Starch, vol. 31, pp. 235–241, 1979.
Yoshiyuki Takasaki, *Production of Maltohexaose by α–Amylase from Bacillus circulans G–6*, Agricultural and Biological Chemistry, vol. 46, pp. 1539–1547, 1982.
Hajime Taniguchi et al, *Enzymic Digestion of Potato Starch Granules*, J. Jap. Soc. Starch Science, vol. 29, pp. 107–116, 1982.
Iwao Maeda et al, *Purification of R–enzyme from Malted Barley and Its Role in in vitro Digestion of Barley Starch Granules*, J. Jap. Soc. Starch Science, vol. 26, pp. 117–127, 1979.
Iwao Maeda et al, *Digestion of Barley Starch Granules by the Combined Action of α–and β–Amylases Purified from Barley and Barley Malt*, Agricultural and Biological Chemistry, vol. 42, pp. 259–267, 1978.
Takaya Hayashi et al, *Production and Purification of New Maltohexaose-forming Amylases from Alkalophilic Bacillus sp. H–167*, Agricultural and Biological Chemistry, vol. 52, pp. 443–448, 1988.

Primary Examiner—Leon B. Lankford, Jr.
Assistant Examiner—Francisco C. Prats
Attorney, Agent, or Firm—Browdy and Neimark

[57] ABSTRACT

Disclosed is a novel amylase which mainly forms maltohexaose and maltoheptaose when acts on starch, but does not substantially hydrolyze maltohexaose and a lower molecular oligosaccharide than maltohexaose. The amylase can be prepared from microorganisms of the genus Alcaligenes, and has a relatively-high optimum temperature and thermal stability, as well as a relatively-wide range of optimum pH and pH stability. By using the amylase, saccharide compositions rich in maltohexaose and/or maltoheptaose or those rich in maltohexaitol and/or maltoheptaitol can be readily prepared in an industrial scale, and the saccharide compositions thus obtained can be used in a variety of food products, cosmetics and pharmaceuticals.

3 Claims, 4 Drawing Sheets

MALTOHEXAOSE AND MALTOHEPTAOSE-FORMING AMYLASE, AND ITS PREPARATION AND USES

This is a division of parent application Ser. No. 08/396,746, filed Mar. 1, 1995 now U.S. Pat. No. 5,527,699.

BACKGROUND OF THE INVENTION

1. Field of the Invention

The present invention relates to a novel maltohexaose and maltoheptaose-forming amylase, and preparation and uses thereof, more particularly, to a maltohexaose and maltoheptaose-forming amylase which mainly forms maltohexaose and maltoheptaose from starch (designated as "AMYLASE" hereinafter) and preparation thereof, as well as microorganisms which produce such an amylase, saccharide compositions containing maltohexaose and/or maltoheptaose produced therewith or those containing maltohexaitol and/or maltoheptaitol obtainable by hydrogenating the maltohexaose and maltoheptaose, and compositions containing these saccharides.

2. Description of the Prior Art

Methods for specifically producing maltooligosaccharides such as maltose and maltotetraose by allowing specific amylases to act on starch have been employed in an industrial scale, and widely used in processes of compositions such as foods and pharmaceuticals. Demands for saccharides containing a relatively-large quantity of maltooligosaccharides such as maltohexaose and maltoheptaose have been increased because, among maltooligosaccharides, those with a relatively-low molecular weight are considerably-low in sweetness, readily digestible and absorbable.

Enzymes or amylases, derived from microorganisms, which produce a relatively-large amount of maltohexaose when act on starch are known, but no amylase which forms maltooligosaccharides higher than maltoheptaose has been known.

Amylases which mainly produce maltohexaose from starch can be roughly classified into two groups based on their actions. The one is an exo-type maltohexaose-forming amylase which hydrolyzes amylaceous substances so as to remove successive maltohexaose units from the non-reducing chain ends, namely, maltohexaohydrolase (EC 3.2.1.98), and the other is an endo-type maltohexaose-forming amylase, namely, endo-type α-amylase (EC 3.2.1.1) which acts on internal amylaceous saccharide chains to produce maltohexaose in a relatively-large quantity.

Kainuma et al. reported in *FEBS Letters*, Vol.26, pp.281–285 (1972) a microorganism of the species *Aerobacter aerogenes* which intracellularly forms an exo-type maltohexaose-forming amylase which is characteristic of its relatively-low optimum temperature and thermal stability, but it is insufficient in heat tolerance for an industrial use.

J. F. Kennedy et al. reported in *Starch*, Vol.31, pp.235–241 (1979) a microorganism of the species *Bacillus subtilis* forms an endo-type maltohexaose-forming amylase, and Takasaki reported in *Agricultural and Biological Chemistry*, Vol.46, pp.1539–1547 (1982) a microorganisms of *Bacillus circulans* G-6 forms such an amylase. Taniguchi reported in *Denpun Kagaku* (Starch Science), Vol.29, pp.107–116 (1982) a microorganism of the species *Bacillus circulans* F-2 forms such an amylase, and Hayashi et al. reported in *Agricultural and Biological Chemistry*, Vol.52, pp.443–448 (1988) a microorganism of the species Bacillus sp. H-167 forms such an amylase. It has been known that, among these amylases produced from such microorganisms, those from *Bacillus circulans* G-6, *Bacillus circulans* F-2 and Bacillus sp. H-167 form maltohexaose from starch in the maximum yield of about 25–30 w/w %, on a dry solid basis (d.s.b.), (the wording "w/w %" is designated as "%" hereinafter, if not specified otherwise), but they do not form maltoheptaose, and further they hydrolyze maltohexaose into maltose and maltotetraose as their enzymatic reactions proceed.

Now referring to amylases derived from microorganisms of the species *Bacillus subtilis*, they only form about 25% maltohexaose from starch and do not hydrolyze maltohexaose. Such amylases are not suitable for an industrial-scale production of high maltohexaose content saccharides because they do not form maltohexaose in a satisfactorily-high yield while forming a relatively-large quantity of lower molecular oligosaccharides under starch saccharification conditions, and because they could not be readily obtained in quantity from microorganisms.

In *Agricultural and Biological Chemistry*, Vol.42, pp.259–267 (1978) reported that a purified α-amylase, prepared from malts, mainly forms maltohexaose and maltoheptaose during the early stage of the enzymatic reaction when acts on starch. It is also reported that the formed maltohexaose and maltoheptaose are decomposed almost completely into lower molecular oligosaccharides such as maltose and maltotetraose as the enzymatic reaction proceeds, and, therefore, it hardly produces saccharified products, mainly containing maltohexaose and maltoheptaose, from starch.

SUMMARY OF THE INVENTION

The present inventors pursued a novel amylase which mainly forms maltohexaose and maltoheptaose from starch and screened microorganisms which form such an amylase and have overcome the object. As a result, they found that a novel microorganism of the genus Alcaligenes or *Alcaligenes latus* D2271, isolated from a soil nearby Komagatake in Yamanashi, Japan, forms a novel amylase which forms a relatively-large quantity of maltohexaose and maltoheptaose from starch (sometimes designated as "AMYLASE" in the specification), established the preparation of saccharide compositions containing maltohexaose and/or maltoheptaose by allowing the amylase to act on amylaceous substances, and also established compositions such as food products, cosmetics, pharmaceuticals and shaped products. Thus, they accomplished this invention.

DETAILED DESCRIPTION OF THE INVENTION

The present invention is to provide a novel amylase which forms a relatively-large quantity of maltohexaose and maltoheptaose from starch but does not substantially decompose the formed maltohexaose and maltoheptaose, and to preparations of saccharide compositions containing maltohexaose and/or maltoheptaose by using the amylase, as well as to uses of the saccharide compositions.

The results of an identification test of the novel microorganism *Alcaligenes latus* D2271 according to the invention are as shown in the below. The test was carried out according to the method as described in *Biseibutsu-no-Bunrui-to-Dotei* (Classification and Identification of Microorganisms), edited by Takeharu Hasegawa, published by Gakkai Publishing Center, Tokyo, Japan (1985).

A. Morphology (1) Characteristics of cells formed when incubated at 27° C. in agar with potato dextrose
Existing in a bacillus form with a size of 0.7–1.3× 1.3–2.4 μm, and usually existing in a single form, but uncommonly existing in a coupled- or linked-form;
Possessing motility, asporogenicity and flagellum;
Non-acid fast;
Gram stain: Negative;
Accumulating poly-β-hydroxy butyrate;

(2) Characteristics of cells formed when incubated at 37° C. in agar with yeast extract and malt extract
Existing in a size of about 0.5–1.0×1.3–2.4 μm after 24-hour incubation, and in a size of about 0.5–1.0× 1.0–2.5 μm after 72-hour incubation;
Existing in a single form;

Cultural property (1) Characteristics of colony formed when incubated at 37° C. in agar plate with potato dextrose
Shape: Circular colony having a diameter of about 1 mm after 24-hour incubation, and about 3–4 mm after 96-hour incubation;
Rim: Entire;
Projection: Umbilicate;
Gloss: Dull;
Surface: Creases-like; and
Color: Opaque, white or ocher;

(2) Characteristics of colony formed when incubated at 37° C. in agar plate with yeast extract and malt extract
Shape: Circular colony having a diameter of about 3–5 mm after 96-hour incubation;
Rim: Entire;
Projection: Half-lens type;
Gloss: Glistening;
Surface: Smooth; end
Color: White or creamy;

(3) Characteristics of colony formed when incubated at 37° C. in slant agar with potato dextrose
Growth: Satisfactory;
Shape: Thread-like;

(4) Characteristics of colony formed when stab cultured at 37° C. in gelatin plate with yeast extract and malt extract
Liquefied;

C. Physiological properties (1) Reduction of nitrate: Positive in succinate medium;

(2) Denitrification reaction: Negative;

(3) Methyl red test: Negative;

(4) VP-test: Negative;

(5) Formation of indole: Negative;

(6) Formation of hydrogen sulfide: Negative;

(7) Hydrolysis of starch: Positive;

(8) Utilization of citric acid: Negative;

(9) Utilization of inorganic nitrogen source: Utilizing ammonium salts and nitrates;

(10) Formation of pigment: Negative;

(11) Urease: Positive;

(12) Oxidase: Positive;

(13) Catalase: Positive;

(14) Growth conditions: Growing at a pH in the range of 5–8 and a temperature in the range of 10°–41° C.;

(15) Oxygen requirements: Aerobic;

(16) Utilization of carbon source and acid formation:

| Carbon source | Utilization | Acid formation |
|---|---|---|
| D-Glucose | + | − |
| D-Galactose | + | − |
| D-Mannose | + | − |
| D-Fructose | + | − |
| L-Arabinose | + | − |
| D-Xylose | + | − |
| L-Rhamnose | + | − |
| Maltose | + | − |
| Sucrose | + | − |
| Lactose | + | − |
| Trehalose | + | − |
| Raffinose | + | − |
| Mannitol | − | − |
| Dextrin | + | − |
| Dulcitol | − | − |

(17) Decarboxylase test on amino acid: Negative against L-lysine, L-arginine and L-ornithine;

(18) DNase: Negative;

(19) Formation of 3-ketolactose: Negative; and (20) Mol % guanine (G) plus cytosine (C) of DNA: 67%.

The bacteriological properties were compared with those of known microorganisms with reference to *Bergey's Manual of Systematic Bacteriology*, Vol.1 (1984). As a result, it was revealed that the microorganism was identified as a microorganism of the species *Alcaligenes latus*.

Based on these results, the present inventors named this microorganism "*Alcaligenes latus* D2271", and deposited it on Feb. 23, 1994, in Fermentation Research Institute, Agency of Industrial Science and Technology, Ibaraki, Japan.

The deposition of the microorganism was accepted on the same day and has been maintained by the institute under the accession number of FERM BP-4578.

In addition to the above-identified microorganism, other strains of the species *Alcaligenes latus* and their mutants can be suitably used in the invention as long as they produce the present AMYLASE.

Any nutrient culture medium can be used in the invention as long as these microorganisms can grow therein and produce the present AMYLASE, and therefore synthetic- and natural-nutrient culture media can be used as a nutrient culture medium. Any carbon-containing substance can be used in the invention as a carbon source as long as it is utilized by the microorganisms: Examples of such carbon sources are saccharides such as maltose, dextrin and starch; and natural substances of saccharides-containing substances such as theriac and yeast extract. The concentration of these carbon sources used in nutrient culture media are appropriately chosen dependently on the type of carbon resources used. For example, preferable concentrations of starch used in media are usually 20% or lower, more particularly, 5% or lower, d.s.b., in view of the growth of microorganisms. The nitrogen sources usable in the invention are, for example, inorganic nitrogen compounds such as ammonium salts and nitrates; and organic nitrogen-containing substances such as urea, corn steep liquor, casein, peptone, yeast extract and beef extract. The inorganic ingredients usable in the invention are, for example, calcium salts, magnesium salts, potassium salts, sodium salts, phosphates and other salts of manganese, zinc, iron, copper, molybdenum and cobalt.

The microorganisms used in the invention are cultured under aerobic conditions at a temperature, usually, in the range of 10°–40° C., preferably, in the range of 25°–37° C., and at a pH in the range of 5–8, preferably, in the range of 6–7.5. The cultivation time used in the invention is set to a time longer than that required for the growth initiation of the microorganisms, preferably, 10–100 hours. The concentration of dissolved oxygen (DO) in nutrient culture media is not specifically restricted, but usually it is set to a level in the range of 0.5–20 ppm. The concentration of DO can be kept within the range by controlling aeration, stirring and aeration with oxygen, and/or increasing the inner pressure of fermenters. The cultivation is carried out batchwise or in continuous manner.

After completion of the cultivation of microorganisms, the present AMYLASE is collected from the resultant cultures. When the activity of the present AMYLASE is present in the resultant nutrient culture media which can be used intact as a crude enzyme. Conventional liquid-solid separation methods can be employed in the invention as a method for separating microorganisms from nutrient culture media. For example, methods for directly centrifuging cultures, filtrating cultures with precoat filters, and separating microorganisms by membrane filtration using plain filters or follow fibers can be suitably used. Cultures free of microorganisms can be used as a crude enzyme, and, preferably, they can be concentrated by conventional manner prior to use: For example, salting out using ammonium sulfate, sedimentation using acetone and alcohol, and concentration using membranes such as plain filters and follow fibers can be used.

Cultures free of microorganisms and concentrates thereof can be immobilized by conventional methods. Examples of such conventional methods are conjugation methods using ion exchangers, covalent bonding- and absorption-methods using resins and membranes, and inclusion methods using high-molecular weight substances.

Crude enzymes can be used without any further treatment or may be purified in usual manner. For example, an enzyme exhibiting a single band on electrophoresis can be prepared by dialyzing crude enzyme preparations which had been prepared by salting out cultures to remove microorganisms with ammonium sulfate and concentrating the resultant solutions. The concentrate was dialyzed, and successively purified on anion-exchange column chromatography using "DEAE TOYOPEARL®", commercialized by Tosoh Corporation, Tokyo, Japan, an anion exchange resin; hydrophobic column chromatography using "BUTYL TOYOPEARL®", commercialized by Tosoh Corporation as described above, a hydrophobic resin; and column chromatography using "PHENYL SUPERROSE® HR5/5", commercialized by Pharmacia LKB Biotechnology AB, Uppsala, Sweden.

The present AMYLASE thus obtained has the following physicochemical properties of:

(1) Acting
Mainly forming maltohexaose and maltoheptaose when acts on starch, but not substantially hydrolyzing lower molecular oligosaccharides than maltohexaose and not substantially acting on maltoheptaose;

(2) Molecular weight
43,000±3,000 daltons on sodium dodecyl sulfate polyacrylamide gel electrophoresis (SDS-PAGE);

(3) Isoelectric point (pI)
7.6±0.5 on isoelectrophoresis using ampholyte;

(4) Optimum pH
About 5.0 in the presence of calcium ion;

(5) Optimum temperature
About 70° C. in the presence of calcium ion;

(6) pH Stability
Stable at a pH in the range of about 4.5–10.5 in the presence of calcium ion;

(7) Thermal stability
Stable up to a temperature of about 60° C. in the presence of calcium ion;

(8) Promotion of activity and stabilization
Being promoted its activity and stabilized by calcium ion;

(9) Inhibition
Being inhibited by copper ion, lead ion, zinc ion, mercury ion and EDTA.

The activity of the present AMYLASE is assayed as follows: 0.2 ml of an enzyme solution is added to 5 ml of 0.3 w/v % soluble starch in 20 mM phosphate buffer (pH 5.5) containing 1 mM $CaCl_2$), and the mixture solution is incubated at 40° C. for 10 min, followed by sampling 0.5 ml of the resultant solution, and adding the solution to 15 ml of 0.02N sulfate solution to suspend the enzymatic reaction. The resultant is mixed with 0.2 ml of 0.1N iodine solution, stirred, allowed to stand at 25° C. for 15 min, and determined its absorbance at a wave length of 660 nm. One unit activity of the present AMYLASE is defined as the amount of enzyme which diminishes the iodine coloration of 15 mg soluble starch when reacted at 40° C. for 10 min.

When used the present AMYLASE to produce saccharide compositions containing maltohexaose and/or maltoheptaose, it is satisfactorily allowed to act on amylaceous substances as a substrate such as starch, amylopectin, amylose and starch hydrolyzates with an industrial view point. If necessary, in the case of producing foods and beverages containing amylaceous substances, the present AMYLASE can be allowed to act on such foods and beverages to form therein maltohexaose and/or maltoheptaose to prevent the retrogradation of the amylaceous substances and to prolong the shelf-life thereof.

The present AMYLASE is added to a solution, which contains about 5–45% amylaceous substances, and, preferably, further contains about 0.5–50 mM calcium salts such as calcium chloride in an amount of 0.5–20 units/g amylaceous substance, d.s.b., followed by the enzymatic reaction at a pH of 3–8 and a temperature of 40–90 for 1–100 hours.

To obtain the highest possible content of maltohexaose and maltoheptaose in reaction mixtures, it is desirable to allow the present AMYLASE to act on starch hydrolysates which were carefully prepared with acids or α-amylase to keep the liquefaction as low as possible, i.e. a DE lower than 10, preferably, a DE lower than 5.

In the present enzymatic reaction, the saccharide compositions comprising maltohexaose and maltoheptaose, and their contents are readily varied and increased by using the present AMYLASE and other amylaceous substance-related enzyme(s) such as cyclomaltodextrin-glucanotransferase (EC 2.4.1.19), α-amylase, (EC 3.2.1.1), β-amylase (EC 3.2.1.2), glucoamylase (EC 3.2.1.3), α-glucosidase (EC 3.2.1.20), pullulanase (EC 3.2.1.41), isoamylase (EC 3.2.1.68) and maltotetraose-forming amylase (EC 3.2.1.60).

To increase the yield of maltohexaose and maltoheptaose is readily feasible by subjecting amylaceous substances to the action of the present AMYLASE together with pullulanase and isoamylase. Maltohexaose and maltoheptaose can be arbitrarily obtained by using the resultant saccharide compositions as a material which contain about 30–50%, d.s.b, of maltohexaose and maltoheptaose in total, and by separating the impurities of saccharides and dextrin.

As an example of the separation methods usable in the invention, a method using a semipermeable membrane as disclosed in Japanese Patent Laid-Open No.4,647/73, a method using a precipitant as disclosed in Japanese Patent Laid-Open No.102,854/74, and a method using a strong-acid cation exchange resin as disclosed in Japanese Patent Laid-Open Nos.148,794/84 can be arbitrarily used. These methods enable the preparation of high maltohexaose content saccharides and high maltoheptaose content saccharides with a purity of 90% or higher, d.s.b. Especially, methods using strong-acid cation exchange resins can be advantageously used in an industrial scale to remove concomitant saccharides and to obtain high maltohexaose and/or maltoheptaose content solutions. In this case, any one of fixed bed-, moving bed- and semi moving-methods can be employed.

Reaction mixtures after enzymatic reaction or solutions prepared by removing concomitant saccharides from the reaction mixtures are in usual manner subjected to filtration and centrifugation to remove insoluble substances, and the resultant solutions are decolored with an activated charcoal, desalted with ion exchangers in H- and OH-form, and concentrated into syrupy products. If necessary, the syrupy products can be readily dried into powdery products by spray-drying method, etc.

The resultant saccharide compositions, containing maltohexaose and/or maltoheptaose, according to the invention usually contain maltohexaose and/or maltoheptaose in an amount of 30% or higher, and, preferably, 40% or higher, d.s.b. Although the properties of the powdery products are varied dependently on the content of maltohexaose and/or maltoheptaose, the products have a substantial non-hygroscopicity, non-solidification and free-flowing ability, and because of these the material- and labor-costs for packaging, transportation and storage can be cut by a large margin.

The powdery products thus obtained have a substantial non-hygroscopicity and a relatively-high thermal tolerance and stability, and because of these they can be arbitrarily used as a filler, excipient, adjuvant and powdery base in a powdery mixed sweetener, instant juice mix, instant soup mix, granule and tablet which have been very difficult to prepare. The powdery products can be also used in an instant pudding mix, instant hot cake mix, confectionery material, bread material and cereal material by substituting them for the part of or the whole of products in powder form such as wheat, corn grits and starch. Saccharide compositions containing maltohexaitol and/or maltoheptaitol with a satisfactorily-high chemical stability can be arbitrarily prepared by hydrogenating saccharide compositions containing maltohexaose and/or maltoheptaose.

For example, a saccharide composition containing maltohexaose and maltoheptaose is prepared into a solution having a concentration of about 40–60%, d.s.b., and the solution is subjected to autoclave, admixed with Raney nickel as a catalyst in an amount of about 8–10%, d.s.b., and heated up to a temperature of 90°–140° C. while stirring, followed by increasing the hydrogen pressure up to 20–150 kg/cm² to terminate the hydrogenation. Thereafter, the raney nickel is removed, and, similarly as in the preparation of saccharide compositions containing maltohexaose and/or maltoheptaose, decolored, desalted, purified and concentrated into syrupy products. If necessary, the syrupy products can be spray-dried into powdery products.

The resultant saccharide compositions containing maltohexaitol and maltoheptaitol usually contain maltohexaitol and maltoheptaitol in an amount not less than 30%, d.s.b. The maltohexaitol and/or maltoheptaitol with a high purity can be readily obtained by fractionation, similarly as in the preparation of maltohexaose and maltoheptaose, comprising removing concomitant saccharides from saccharide compositions containing maltohexaitol and/or maltoheptaitol as a material.

The above-mentioned saccharide compositions containing maltohexaose and/or maltoheptaose, or those containing maltohexaitol and/or maltoheptaitol can be arbitrarily used as a low sweetener, filler, viscosity-controlling agent, moisture-retaining agent, gloss-imparting agent, flavor-preserving agent, crystallization-preventing agent, stickiness-preventing agent for candy, and starch retrogradation-preventing agent. The saccharide compositions can be arbitrarily used in foods, beverages, feeds, cosmetics, pharmaceuticals and shaped products as an energy-supplementing agent, and also used in a variety of compositions such as household commodities, materials for agriculture and forestry, chemical reagents, and materials for chemical industry.

Although the saccharide compositions containing maltohexaose and/or maltoheptaose or those containing maltohexaitol and/or maltoheptaitol have a relatively-low sweetness, they can be used intact as a seasoning for sweetening. If necessary, they can be used together with adequate amounts of one or more other sweeteners, for example, powdered syrup, glucose, maltose, sucrose, isomerized sugar, honey, maple sugar, sorbitol, maltitol, lactitol, dihydrocharcone, stevioside, α-glycosyl stevioside, rebaudioside, glycyrrhizin, L-aspartyl L-phenylalanine methyl ester, saccharin, glycine and alanine; and/or a filler such as dextrin, starch or lactose.

The saccharide compositions containing maltohexaose and/or maltoheptaose or those containing maltohexaitol and/or maltoheptaitol have the following features: (i) They have a sweetness which well harmonizes with other materials having sour-, acid-, salty-, bitter-, astringent- and delicious-tastes; and (ii) they are highly acid- and heat-resistant. Thus, they can be favorably used in food products in general as a sweetener, taste-improving agent or quality-improving agent.

The saccharide compositions containing maltohexaose and/or maltoheptaose or those containing maltohexaitol and/or maltoheptaitol can be used in seasonings such as soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "takuan-zuke-no-moto" (a premix for pickled radish), "hakusai-zuke-no-moto" (a premix for fresh white rape pickles), "yakiniku-no-tare" (a sauce for Japanese grilled meat), curry roux, instant stew mix, instant soup mix, "dashi-no-moto" (an instant stock mix), nucleic acid condiments, mixed seasoning, "mirin" (a sweet sake), "shin-mirin" (a synthetic mirin), table sugar and coffee sugar. Also, the saccharide containing maltohexaose and/or maltoheptaose or the saccharide containing maltohexaitol and/or maltoheptaitol can be freely used for sweetening "wagashi" (Japanese cake) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products; canned and bottled products such as those of meat, fish meat, fruit and vegetable; alcoholic beverages such as refined sake, synthetic sake, liqueur and foreign wines; soft drinks such as tea, coffee, cocoa, juice, carbonated beverage, sour milk beverage and beverage containing a lactic acid bacterium; instant hot cake mix and "sokuseki-shiruko" (an instant mix of adzuki-bean soup with rice cake), and instant soup mix; and beverages such as baby foods, foods for therapy, beverages supplemented with nutrition, peptide foods and frozen foods; as well as for improving the tastes and qualities of the aforementioned food-products.

The present saccharide compositions containing maltohexaose and/or maltoheptaose or those containing maltohexaitol and/or maltoheptaitol can be also used in feeds and pet foods for domestic animals, poultry and fishes to improve their taste preferences. These saccharide compositions can be arbitrarily used as a sweetener, taste-improving agent or quality-improving agent in other products in the form of a solid, paste or liquid such as a tobacco, cigarette, dentifrice, lipstick, rouge, lip cream, internal medicine, tablet, troche, cod liver oil in the form of drop, cachou, oral refrigerant, gargle, cosmetics or pharmaceutical.

The present saccharide compositions containing maltohexaose and/or maltoheptaose or those containing maltohexaitol and/or maltoheptaitol can be used as a quality-improving agent or a stabilizer for biologically active substances susceptible to lose their effective ingredients and activities, as well as in health foods and pharmaceuticals containing biologically active substances. Examples of such biologically active substances are lymphokines such as α-, β- and γ-interferons, tumor necrosis factor-α (TNF-α), tumor necrosis factor-β (TNF-β), macrophage migration inhibitory factor and interleukin 2; hormones such as insulin, growth hormone, prolactin, erythropoietin, follicle-stimulating hormone and placental hormone; biological preparations such as BCG vaccine, Japanese encephalitis vaccine, measles vaccine, live polio vaccine, smallpox vaccine, tetanus toxoid, Antivenenum Trimeresurus flavoviridis and human immunoglobulin; antibiotics such as penicillin, erythromycin, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease, β-amylase, isoamylase, glucanase and lactose; extracts such as ginseng extract, snapping turtle extract, chlorella extract, aloe extract and propolis extract; viable microorganisms such as viruses, lactic acid bacteria and yeasts; and other biologically active substances such as royal jelly. By using the present saccharide compositions containing maltohexaose and/or maltoheptaose or those containing maltohexaitol and/or maltoheptaitol, the aforementioned biologically active substances are arbitrarily prepared into health foods and pharmaceuticals with a satisfactorily-high stability and quality without fear of losing or inactivating their effective ingredients and activities.

As is described above, the saccharide compositions in the present invention can be arbitrary used in orally or parenterally administrable foods, beverages, cosmetics and pharmaceuticals, as well as in household commodities, materials for agriculture and forestry, chemical reagents, and materials for chemical industry.

Methods to incorporate into above-mentioned products the present saccharide compositions containing maltohexaose and/or maltoheptaose or those containing maltohexaitol and/or maltoheptaitol are conventional ones, for example, mixing, dissolving, soaking, permeating, sprinkling, applying, spraying, injecting and solidifying as long as the incorporation is attained before completion of their processings. Although the amount of these saccharide compositions to be incorporated into is varied dependently on the compositions used, it is usually 0.1% or higher, preferably, 0.5% or higher with respect to maltohexaose, maltoheptaose, maltohexaitol and maltoheptaitol, d.s.b. The following experiments explain the present invention in more detail:

EXPERIMENT 1

Production of the Enzyme

A liquid nutrient culture medium, consisting of 2.0 w/v % soluble starch, 0.5 w/v % peptone, 0.1 w/v % yeast extract, 0.1 w/v % potassium diphosphate, 0.06 w/v % sodium phosphate dihydrate, 0.05 w/v % magnesium sulfate heptahydrate, 0.5 w/v % calcium carbonate and water, was placed in 500-ml Erlenmeyer flasks about 100-ml aliquots, and autoclaved at 121° C. for 15 min to effect sterilization, cooled, inoculated with a stock culture of *Alcaligenes latus* D2271 (FERM BP-4578), and incubated at 37° C. for 20 hours under stirring and shaking conditions of 200 rpm. The resultant cultures were pooled and used as a seed culture.

About 20 L of a fresh preparation of the same nutrient culture medium used in the above culture was placed in a 30 L fermenter, sterilized, cooled to 37° C., inoculated with one v/v % of the seed culture, and incubated for about 24 hours while stirring under aerobic conditions at 37° C. About 19 L of the culture was centrifuged to obtain about 18 L of culture supernatant. The AMYLASE activity of the resultant culture supernatant was about 58 units/ml.

EXPERIMENT 2

Purification of Enzyme

The culture supernatant obtained in Experiment 1 was subjected to UF-membrane filtration to obtain about 800 ml of the concentrated enzyme solution having 1,200 units/ml of the AMYLASE. Three hundred ml of the resultant enzyme concentrate was dialyzed against 10 mM Tris-HCl buffer (pH 8.0) containing 5 mM calcium chloride for 24 hours, and centrifuged to remove insoluble substances. Four hundred ml of the resultant dialyzed supernatant was subjected to column chromatography using a column packed with 100 ml of "DEAE-TOYOPEARL® 650", an ion-exchanger.

The present AMYLASE did not adsorb on the ion-exchanger, and the activity was found in non-adsorbed fractions. The fractions having the objective enzyme activity were pooled, and dialyzed against a fresh preparation of the same buffer containing 0.5M ammonium sulfate. The dialyzed solution thus obtained was centrifuged to remove insoluble substances, and the resultant supernatant was subjected to hydrophobic column chromatography using a column packed with 100 ml of "BUTYL-TOYOPEARL® 650", a hydrophobic gel. The enzyme adsorbed on the gel was eluted from the column with a linear gradient buffer raging from 0.5M to 0M, followed by recovering fractions with the enzyme activity. The resultant fractions were subjected to hydrophobic column chromatography using "PHE-NYL SUPERROSE® HR5/5", followed by recovering fractions with the enzyme activity.

The yield of the purified enzyme preparation obtained in the above was about 25% with respect to the culture supernatant. The specific activity of the purified enzyme preparation was about 1,860 units/mg protein. The protein was determined for its quantity by the Lowry method using bovine serum albumin as a standard. The purified enzyme preparation was determined for its purity on electrophoresis using 7.5 w/v % polyacrylamide gel to exhibit a single protein band, and this revealed that the preparation was an electrophoretically homogeneous enzyme with a relatively-high purity.

EXPERIMENT 3

Property of Enzyme

The AMYLASE preparation obtained in Experiment 3 was subjected to electrophoresis using 10 w/v % sodium dodecyl sulfate polyacrylamide gel, and this revealed that the molecular weight was about 43,000±3,000 daltons in comparison with those of marker proteins commercialized by Japan Bio-Rad Laboratories, Tokyo, Japan.

The purified AMYLASE preparation was subjected to isoelectrophoresis using polyacrylamide gel containing 2 w/v % "AMPHOLINE", an ampholyte commercialized by Pharmacia LKB Biotechnology AB, Uppsala, Sweden. The resultant gel was determined for its pH to reveal that the enzyme has a pI of about 7.6±0.5.

Figure 1:
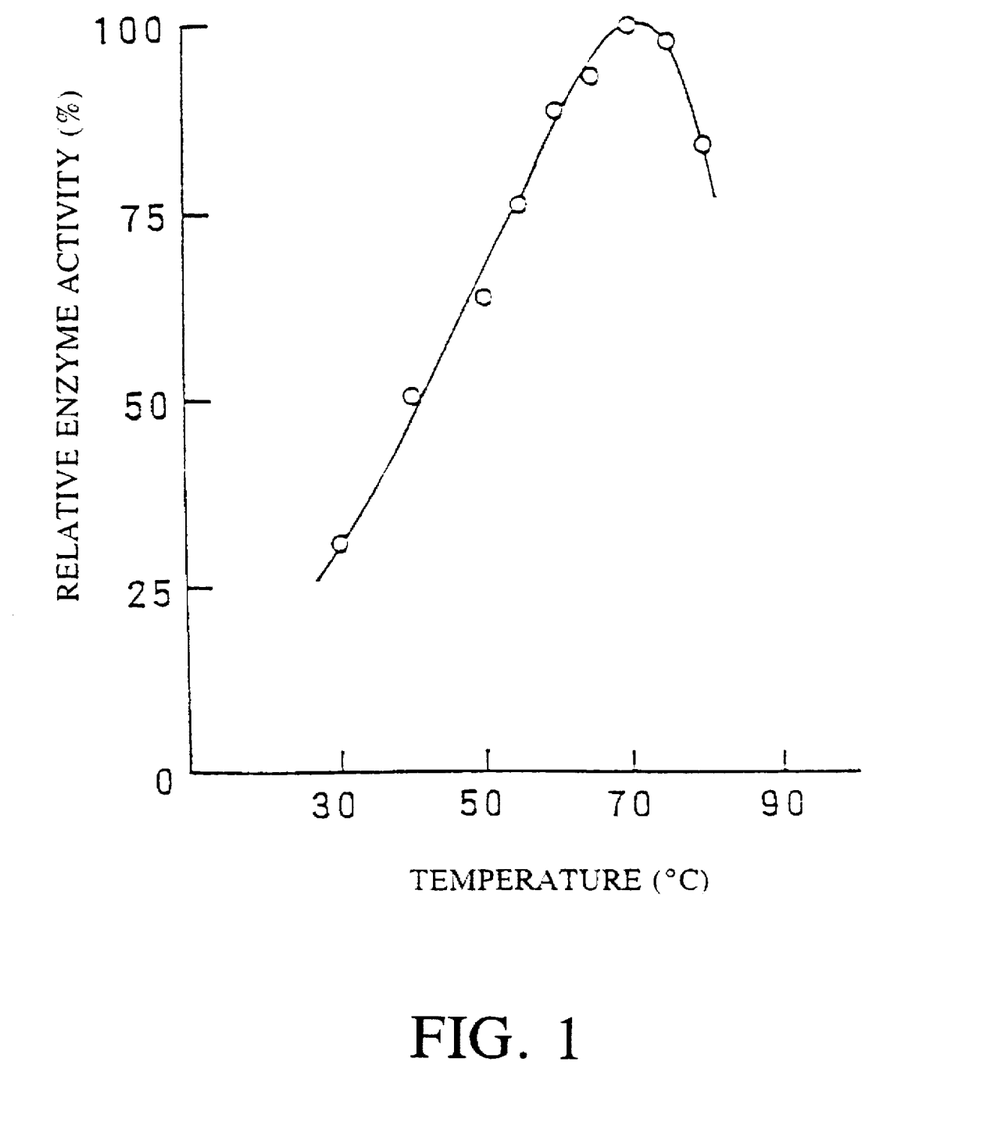
FIG. 1 illustrates the influence of temperature on the activity of the present AMYLASE.
Figure 2:
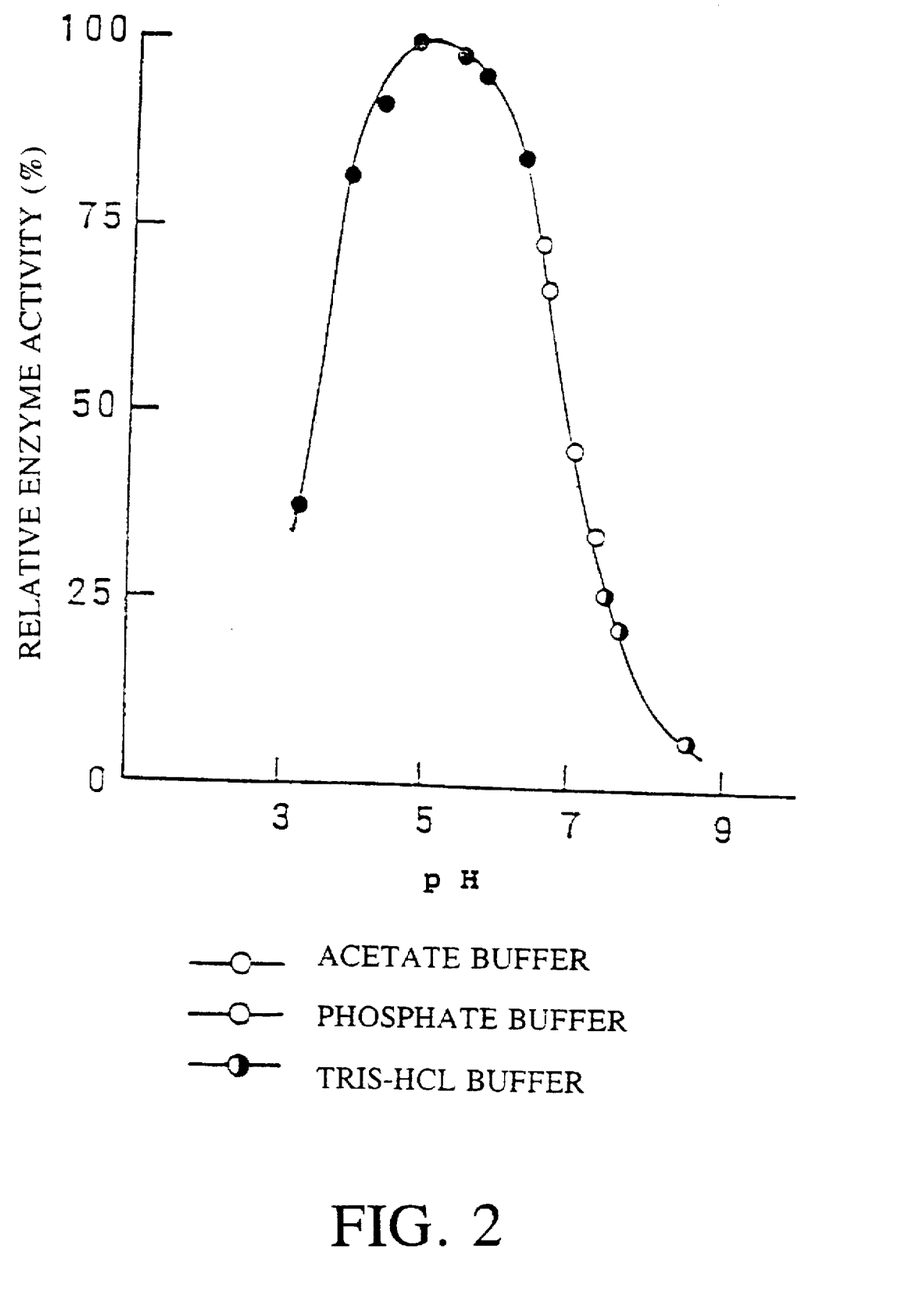
FIG. 2 illustrates the influence of pH on the activity of the present AMYLASE.
Figure 3:
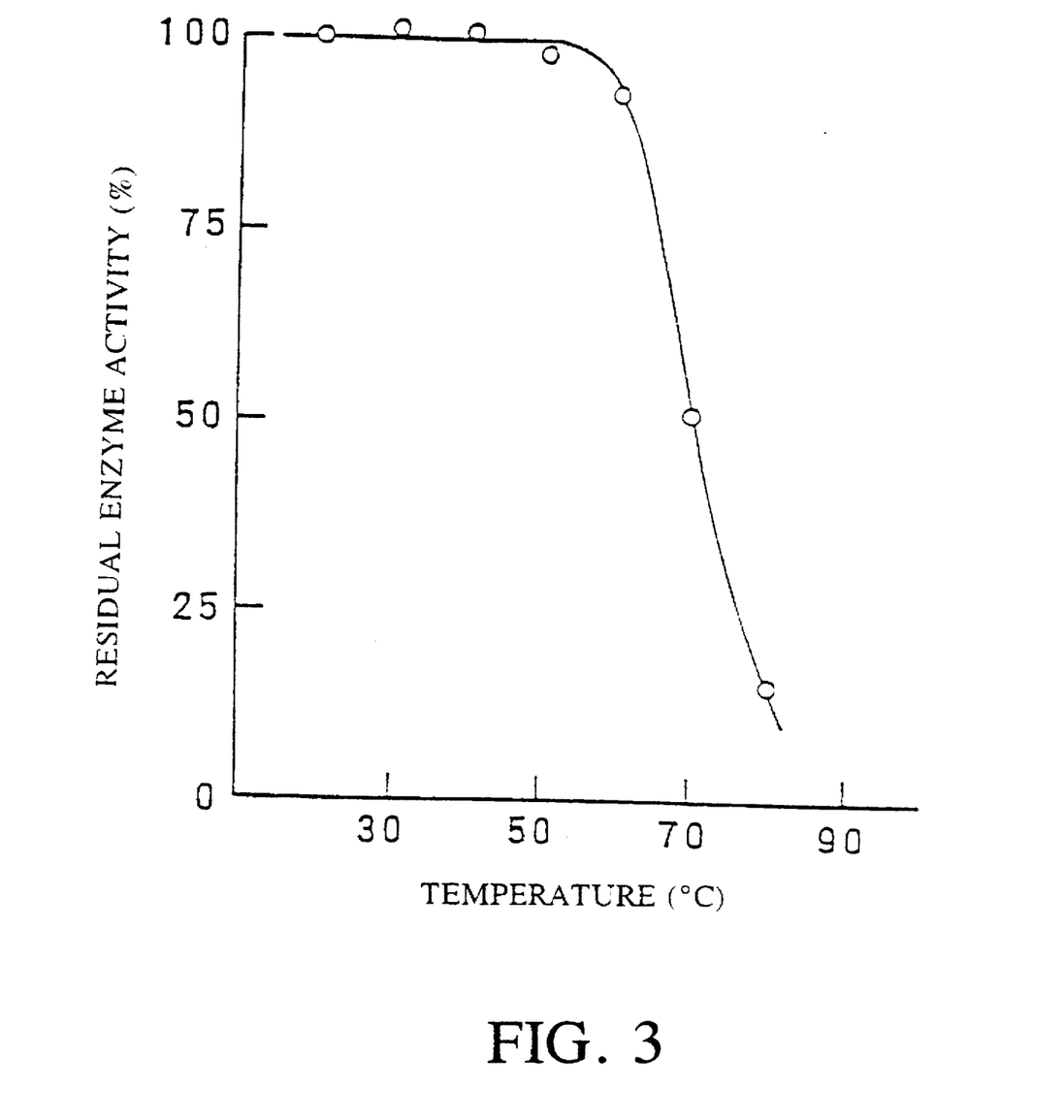
FIG. 3 illustrates the influence of temperature on the stability of the present AMYLASE.
Figure 4:
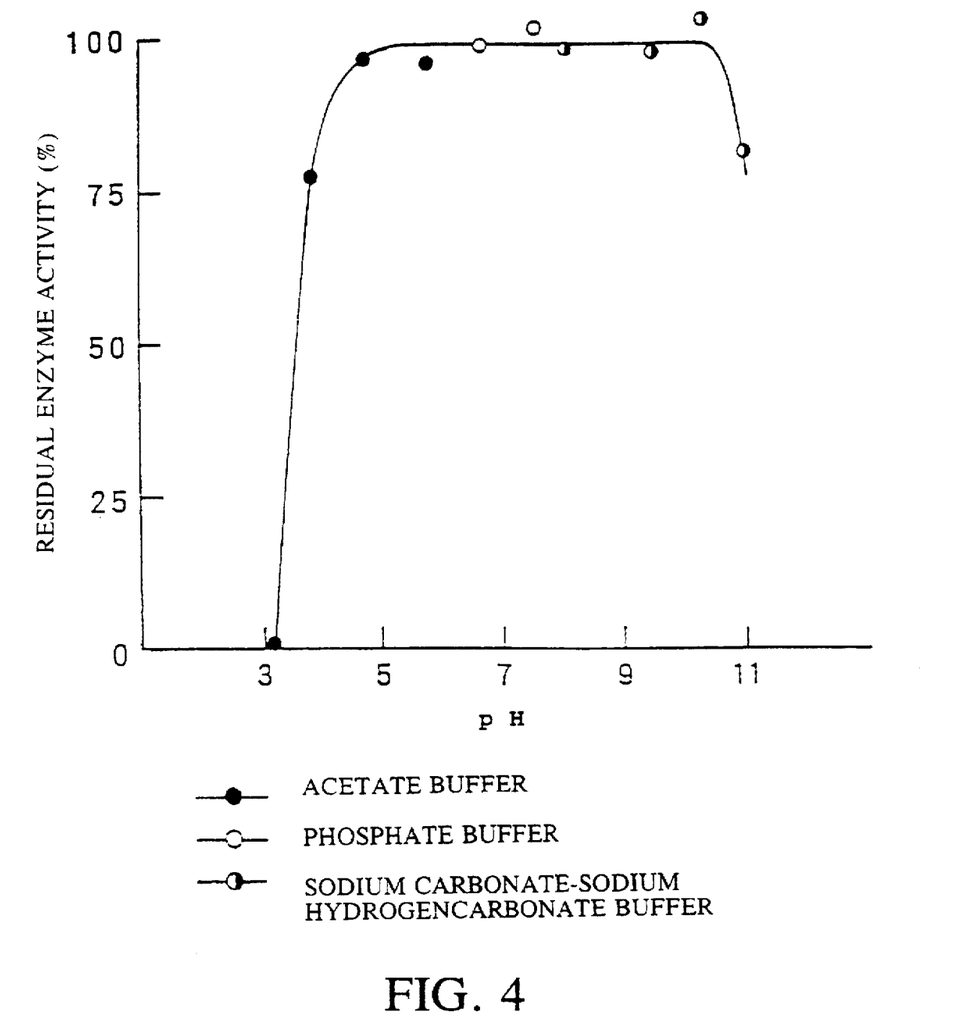
FIG. 4 illustrates the influence of pH on the stability of the present AMYLASE.

Effects of temperature and pH on the enzyme activity were studied in the presence of calcium chloride in accordance with the assay as used for determining the enzyme activity. These results were respectively shown in FIGS. 1 and 2. The optimum temperature was about 70° C., and the optimum pH was about 5.0. The thermal stability of the enzyme was determined by incubating it in 20 mM acetate buffer containing 5 mM calcium chloride (pH 6.0) at different temperatures for 60 min, cooling the buffers, and assaying the remaining enzyme activity in each buffer. The pH stability of the enzyme was determined by incubating it in 20 mM acetate buffer having different pHs at 40° C. for one hour, adjusting the buffer to pH 6.0, and assaying the remaining enzyme activity in each buffer. The results of thermal- and pH-stabilities were respectively shown in FIGS. 3 and 4. The enzyme was stable up to a temperature of about 60° C. and at a pH of about 4.5–10.5. The enzyme was an amylase which does not exhibit a starch-hydrolyzing activity, but has a relatively-high dependency on calcium ion in solutions containing substrates. The enzyme activity was inhibited in the presence of one mM copper ion, lead ion, zinc ion or mercury ion, or by 10 mM EDTA.

EXPERIMENT 4

Activity on Starch

To soluble starch having a final concentration of 2 w/v % in 20 mM acetate buffer (pH 5.5) containing 5 mM calcium chloride was added 50 units/g starch of the purified AMYLASE obtained in Experiment 2, and the mixture solution was subjected to an enzymatic reaction at 40° C., followed by sampling the reaction solution at a prescribed time interval and heating the samples at 100° C. for 10 min to inactivate the remaining enzyme. The resultant reaction solution was analyzed for its hydrolysis rate, blue value and saccharide composition.

The hydrolysis rate was determined by quantifying the total sugar content of the reaction mixture with the anthrone-sulfuric acid reaction method, quantifying the reducing sugar content of the reaction mixture in terms of glucose with the Somogyi-Nelson's method, and calculating the ratio of the reducing sugar content against the total sugar content. The blue value was determined by adding 0.1 ml of the reaction mixture to 15 ml of 0.05N aqueous sulfuric acid solution, mixing the resultant, adding 0.2 ml of 0.1N iodine solution to the resultant solution to develop color, determining the relative absorbance at 660 nm for an iodine color degree, and calculating the percentage of the iodine color degree of each reaction solution at each reaction time to the initial iodine color degree at a reaction time 0.

The saccharide composition was determined by first desalting the reaction mixture, then analyzing the desalted solution on high-performance liquid chromatography (abbreviated as "HPLC" hereinafter). The system and conditions used in the analysis were CCPD system, an apparatus for HPLC commercialized by Tosoh Corporation, Tokyo, Japan, "MCI GEL CK04SS (10 mm⌀×200 mm)", a column for analysis commercialized by Mitsubishi Chemical Corporation, Tokyo, Japan, a flow rate of 0.2 ml/min as an eluant, and a differential refractometer as a detector. The results were as shown in Tables 1 and 2.

TABLE 1

| Reaction time (min) | Hydrolysis rate (%) | Iodine color degree (%) |
|---|---|---|
| 0 | 1.9 | 100 |
| 5 | 3.6 | 45 |
| 10 | 5.3 | 19 |
| 20 | 8.0 | 4.5 |
| 30 | 9.8 | 2.0 |
| 60 | 13.4 | 1.0 |
| 90 | 14.7 | 0.9 |
| 120 | 15.7 | 0.9 |

TABLE 2

| Reaction time (min) | Saccharide composition (%) | | | | | | | |
|---|---|---|---|---|---|---|---|---|
| | G1 | G2 | G3 | G4 | G5 | G6 | G7 | ≧G8 |
| 5 | 0.0 | 0.0 | 0.2 | 0.2 | 0.3 | 2.1 | 2.2 | 95.0 |
| 10 | 0.0 | 0.7 | 0.9 | 0.7 | 1.0 | 3.9 | 4.0 | 88.8 |
| 20 | 0.0 | 1.5 | 2.0 | 1.8 | 1.8 | 7.9 | 7.8 | 77.2 |
| 30 | 0.0 | 2.7 | 3.3 | 2.7 | 2.6 | 11.7 | 11.0 | 66.0 |
| 60 | 0.0 | 6.0 | 6.0 | 4.3 | 3.8 | 19.4 | 16.1 | 44.4 |
| 90 | 0.4 | 8.5 | 7.1 | 4.8 | 4.2 | 25.4 | 18.8 | 30.8 |
| 120 | 0.7 | 10.1 | 8.4 | 4.5 | 4.0 | 25.7 | 19.3 | 27.3 |

As is evident from the results in Table 1, it was revealed that the present AMYLASE was an endo-type amylase because the level of the reduction rate was larger than that of the increment of the hydrolysis rate of starch, and because lower molecular weight oligosaccharides such as maltose and maltotriose were found from the initiation of the enzymatic reaction even if the amount was low. More particularly, the AMYLASE was revealed to be an endo-type α-amylase based on the result of the finding that the anomer type of the formed products was α-form when examined on the optical rotation of anomer type.

As is evident from the results in Table 2, it was revealed that the present starch-hydrolyzing enzyme is a novel α-amylase, a type of enzyme which inherently forms maltohexaose and maltoheptaose when acts on starch, because of the fact that it formed a larger amount of maltohexaose and maltoheptaose than other oligosaccharides from the initiation of the enzymatic reaction while increasing the formation level as the enzymatic reaction proceeded and not decreasing the formation level even if the enzymatic reaction was prolonged. The total yield of maltohexaose and maltoheptaose from starch was about 45%, d.s.b.

EXPERIMENT 5

Substrate Specificity

Fifty units/g substrate, d.s.b., of a purified present AMYLASE obtained by the method in Experiment 2 was added to a substrate with a final concentration of 2 w/v % amylose, amylopectin, glycogen, α-cyclodextrin, β-cyclodextrin, γ-cyclodextrin, pullulan, dextran, glucose, maltose, maltotriose, maltotetraose, maltopentaose, maltohexaose or maltoheptaose, and the mixture was allowed to react at 40° C. and pH 5.5 for 2 hours in the presence of 5 mM calcium chloride. The reaction mixtures before and after the enzymatic reaction were subjected to thin layer chromatography (abbreviated as "TLC" hereinafter) using "KIESEL GEL 60", an aluminum plate (20×20 cm) commercialized by E. Merck, Darmstadt, Germany, to examine whether the enzyme acted on the saccharides as a substrate. TLC was developed once at ambient temperature by using a developing solvent of 1-butanol:pyridine:water=6:4:1 by volume. The development of colorization was effected by spraying to the plates a solution of 20 v/v % sulfuric acid in methanol and heating the plates at 110° C. for 10 min.

As a result, it was found that the present AMYLASE mainly formed maltohexaose and maltoheptaose when acted on amylose, amylopectin and glycogen as a substrate similarly as in soluble starch, but substantially did not act on maltoheptaose even though it slightly formed glucose and maltohexaose as a hydrolysate, and did not act on α-cyclodextrin, β-cyclodextrin, γ-cyclodextrin, pullulan, dextran, glucose, maltose, maltotriose, maltotetraose, maltopentaose and maltohexaose.

EXPERIMENT 6

Acute Toxicity Test

A powdery saccharide product rich in maltohexaose or maltoheptaose which was obtained by the method in Example A-7, and a syrupy product rich in maltohexaitol or maltoheptaitol which was obtained by the method in Example A-8 were respectively administered to mice orally for their acute toxicity test. As a result, it was revealed that these saccharides were relatively-low in toxicity and no mouse died even when administered with the highest possible dose. Therefore, though not so accurate, the value of $LD_{50}$ of the saccharides was 50 g/kg or higher.

The following Examples A illustrate the preparation of the present AMYLASE, saccharide compositions containing maltohexaose and/or maltoheptaose prepared by using the AMYLASE, and preparation of saccharide compositions containing maltohexaitol and/or maltoheptaitol. Examples B illustrate compositions containing one or more of these saccharides.

EXAMPLE A-1

In accordance with the method in Experiment 1, a seed culture of *Alcaligenes latus* D2271 (FERM BP-4578) was inoculated in a fresh preparation of the same nutrient culture medium as used in Experiment 1 and cultured in a fermenter for 30 hours under agitation-aeration conditions except for culturing the microorganism at 30° C. The activity of the present AMYLASE in the resultant supernatant was 66 units/ml of the culture. The culture was filtered with an MF-membrane, and the filtrate was concentrated with a UF-membrane to obtain a concentrated enzyme solution containing about 1,300 units/ml of the present AMYLASE in a yield of about 82% against the activity of the initial culture.

EXAMPLE A-2

Five % suspension (pH 5.5) of potato starch, d.s.b, was gelatinized by heating, cooled to 70° C., admixed with calcium chloride to give 0.02%, mixed with 2 units/g starch of the AMYLASE in Example A-1, liquefied and saccharified for 20 hours. The resultant mixture was autoclaved at 120° C. for 20 min to inactivate the remaining enzyme, cooled, decolored and filtered by an active charcoal, desalted with ion-exchange resins in H- and OH-form, purified and concentrated into a 75% syrup in yield of about 95% to the material, d.s.b.

The product contained 24.2% maltohexaose and 17.7% maltoheptaose, d.s.b, and had a sweetening power of about 15% of that of sucrose. The product can be arbitrarily used in a variety of compositions such as foods, beverages, cosmetics, pharmaceuticals and shaped products as a low sweetener, shape-imparting agent, viscosity-controlling agent, moisture-retaining agent, gloss-imparting agent, adhesive, flavor-imparting agent, crystallization-preventing agent, and stickiness-preventing agent for candy.

EXAMPLE A-3

Ten % suspension (pH 4.5) of potato starch, d.s.b, was gelatinized by heating, cooled to 50° C., mixed with 1,000 units/g starch of isoamylase commercialized by Hayashibara Biochemical Laboratories, Inc., Okayama, Japan, and enzymatically reacted for 20 hours. The resultant mixture was adjusted to pH 5.2, autoclaved at 120° C. for 10 min, cooled to 70° C., admixed with calcium chloride to give a concentration of 0.02%, d.s.b, admixed with 5 units/g starch, d.s.b., of the present AMYLASE prepared in Example A-1, liquefied and saccharified for 8 hours. The reaction solution was autoclaved at 120° C. for 20 min, cooled, and, similarly as in the Example A-2, purified and concentrated to obtain a syrupy product with a concentration of 75% in a yield of about 93% to the material, d.s.b. The saccharide composition consisted of 40.3% oligosaccharides having a degree of glucose polymerization of 5 or lower, 27.3% maltohexaose, 19.2% maltoheptaose, and dextrin having a degree of glucose polymerization of 8 or higher 13.2%, d.s.b. Similarly as the product in Example A-2, the product can be arbitrarily used as a sweetener with a relatively-low sweetness and relatively-low sugar content in a variety of compositions such as foods, beverages, cosmetics, pharmaceuticals and shaped products.

EXAMPLE A-4

Thirty-three % suspension of corn starch, d.s.b., was mixed with calcium carbonate to give a final concentration of 0.1%, d.s.b., and the resultant mixture was adjusted to pH 6.0, admixed with 0.2% per g starch, d.s.b., of "TERMAMYL® 60 L", α-amylase commercialized by Novo Industri A/S Copenhagen Denmark, and subjected to an enzymatic reaction at 95° C. for 15 min. The reaction mixture was autoclaved at 120° C. for 30 min, cooled to 50° C., admixed with 500 units/g starch of isoamylase commercialized by Hayashibara Biochemical Laboratories Inc., Okayama, Japan, and 1.8 units/g starch of the present AMYLASE prepared in the Example A-1, and subjected to an enzymatic reaction for 40 hours. The reaction mixture was similarly as in Example A-2 heated, cooled, purified, concentrated and spray-dried to obtain a powdery composition containing maltohexaose and maltoheptaose having a moisture content lower than 2% in a yield of about 90%, d.s.b.

The saccharide composition consisted of 38.8% oligosaccharides having a degree of glucose polymerization of 5 or lower, 26.7% maltohexaose, 15.7% maltoheptaose, and 18.8% dextrin having a degree of glucose polymerization of 8 or higher. Similarly as the product in Example A-2, the product can be arbitrarily used as a sweetener with a relatively-low sweetness and relatively-low sugar content in a variety of compositions such as foods, beverages, cosmetics, pharmaceuticals and shaped products.

EXAMPLE A-5

A saccharide composition containing maltohexaose and maltoheptaose, obtained by the method in Example A-3, was column chromatographed by using a strong-acid cation exchange resin for fractionation to increase the content of maltohexaose and maltoheptaose. Thus, the saccharide composition was concentrated into 55 w/w % solution as a material saccharide solution. "DIAION SK 104 (K$^+$-form, polymerization degree of 4%)" a resin commercialized by Mitsubishi Chemical Corporation, Tokyo, Japan, was packed in 4 jacketed-stainless steel columns having an inner diameter of 5.4 cm, and the columns were cascaded in series to give a total gel-bed depth of 20 m. The columns were heated to give the inner column temperature of 60° C., and fed with 7 v/v % of the saccharide solution while keeping at the temperature, followed by fractionating the saccharide solution by feeding to the columns with 60° C. hot water at a flow rate of SV (space velocity) 0.12 and collecting fractions containing 35% or higher of maltohexaose or 25% or higher of maltoheptaose. The fractions were pooled, purified and concentrated similarly as in Example A-2 to obtain a syrupy saccharide composition rich in maltohexaose and maltoheptaose in a yield of about 50% to the material saccharide solution, d.s.b. The product contained about 45% maltohexaose and about 31% maltoheptaose, d.s.b, and the sweetening power was less than 10% of that of sucrose. Similarly as in Example A-2, the product can be arbitrarily used as a sweetener with less sweetness and sugar content in a variety of compositions such as foods, beverages, cosmetics, pharmaceuticals and shaped products.

EXAMPLE A-6

A syrupy saccharide composition rich in maltohexaose and maltoheptaose, obtained by the method in Example A-5, was spray-dried to obtain a powdery saccharide composition with a moisture content less than about 2% and rich in maltohexaose and maltoheptaose in a yield of about 98% syrup, d.s.b. Similarly as in Example A-2, the product can be arbitrarily used as a sweetener with less sweetness and sugar content in a variety of compositions such as foods, beverages, cosmetics, pharmaceuticals and shaped products.

EXAMPLE A-7

A saccharide composition rich in maltohexaose and maltoheptaose, obtained by the method in Example A-5, was prepared into a 50% solution which was used as a material saccharide solution. "DIAION SK 104 (K$^+$-form, polymerization degree of 4%)", a strong-acid cation exchanger commercialized by Mitsubishi Chemical Corporation, Tokyo, Japan, was used as a resin for fractionation and packed similarly as in Example A-5 to column. The column was heated to give the inner column temperature of 60° C., and fed with 5 v/v % of the saccharide solution while keeping at the temperature, and the saccharide solution was fractionated by feeding to the column with 60° C. hot water to separatory collect fractions containing 80% or higher of maltohexaose and fractions containing 70% or higher of maltoheptaose, d.s.b. The fractions were respectively pooled, purified, concentrated and spray-dried into a powdery saccharide composition rich in maltohexaose and a powdery saccharide composition rich in maltoheptaose having a moisture content less than about 2% in a yield of about 30% and about 20%, d.s.b., respectively.

The purities of the powdery saccharide composition rich in maltohexaose and the powdery saccharide composition rich in maltoheptaose were about 89% and about 81%, d.s.b., and their sweetening powers were less than 10% of that of sucrose. Similarly as in Example A-2, the products can be arbitrarily used as a sweetener with less sweetness and sugar content in a variety of compositions such as foods, beverages, cosmetics, pharmaceuticals and shaped products.

EXAMPLE A-8

A syrupy saccharide composition containing maltohexaose and maltoheptaose, obtained by the method of Example A-3, was prepared into a 50% solution which was then placed in an autoclave, admixed with 10% raney nickel as a catalyst, and heated up to a temperature of 90°–125° C. while stirring, followed by increasing hydrogen pressure to 20–100 kg/cm$^2$ to terminate hydrogenation. Thereafter, the raney nickel was removed from the reaction mixture, and, similarly as in Example A-2, the reaction mixture was purified and concentrated to obtain a saccharide composition containing maltohexaitol and maltoheptaitol having a moisture content of 25% in a yield of about 90% syrup, d.s.b.

The product contains 27% maltohexaitol, 19% maltoheptaitol, d.s.b, and the sweetening power was about 20% of that of sucrose. The product can be arbitrarily used in a variety of food products as a sweetener with less sweetness and sugar content, body-imparting agent, viscosity-controlling agent, moisture-retaining agent, gloss-imparting agent, adhesive, flavor-imparting agent, crystallization-preventing agent, and stickiness-preventing agent for candy.

EXAMPLE A-9

A saccharide composition rich in maltohexaose and maltoheptaose, obtained by the method in Example A-5, was hydrogenated by the method in Example A-8, and the resultant was purified and concentrated into a 50% saccharide solution rich in maltohexaitol and maltoheptaitol. A saccharide solution thus obtained was column chromatographed in accordance with the method in Example A-7 by using a strong-acid cation exchange resin to separatory collect fractions containing 80% or higher of maltohexaitol and fractions containing 70% or higher of maltoheptaitol, which were then respectively pooled, purified and concentrated into a saccharide syrup rich in maltohexaitol and a saccharide syrup rich in maltoheptaitol, both of which had a concentration of about 75% and obtained in yields of about 30% and about 20%, d.s.b., respectively The purities of the saccharide syrups thus obtained were respectively about 90% and about 82%, d.s.b., and their sweetening powers were less than 10% of that of sucrose. Similarly as in Example A-2, the product can be arbitrarily used as a sweetener with less sweetness and sugar content in a variety of compositions such as foods, beverages, cosmetics, pharmaceuticals and shaped products.

EXAMPLE B-1

Sweetener

One part by weight of a syrupy saccharide composition containing maltohexaose and maltoheptaose, obtained by the method in Example A-2, was homogeneously admixed with 0.02 parts by weight of "αG Sweet", α-glycosyl stevioside commercialized by Toyo Sugar Refining Co., Ltd., Tokyo, Japan, to obtain a syrupy sweetener. The product had a satisfactory sweetness and a 2-fold higher sweetening power of sucrose, and the caloric value was lowered to about ½ of that of sucrose. Because of this, it can be suitably used as a low-caloric sweetener for low-caloric food products for fat persons and diabetics who are restricted to a reduced calorie intake. The product scarcely forms acids and insoluble glucans when dental carries-inducing microorganisms act on it, and this renders it useful for sweetening food products directed to prevent dental carries.

EXAMPLE B-2

Custard Cream

Five hundred parts by weight of corn starch, 400 parts by weight of a powdery saccharide composition rich in maltohexaose and maltoheptaose, 500 parts by weight of maltose, and 5 parts by weight of salt were passed through a sieve to homogeneity. The resultant mixture was admixed with 1,400 parts by weight of egg, and gradually mixed with 5,000 parts by weight of a boiling milk. The mixture thus obtained was continued stirring while heating, and the heating was stopped when the corn starch in the mixture was completely gelatinized to give the whole contents semitransparent, followed by cooling the resultant and adding thereto an adequate amount of a vanilla flavor. The product has a smooth surface and gloss, as well as a mild taste and sweetness.

EXAMPLE B-3

Sweet Rice Jelly (Uiro)

Ninety parts by weight of rice powder, 20 parts by weight of corn starch, 20 parts by weight of sugar, one part by weight of a powdered green tea, an adequate amount of water, and 90 parts by weight of a syrupy saccharide composition containing maltohexaitol and maltoheptaitol, obtained by the method in Experiment A-8, were kneaded to homogeneity. The resultant mixture was placed in a vessel and steamed for 60 min to obtain a rice jelly with powdered green tea. The product has a satisfiable gloss, biting property and flavor. The retrogradation of starch in the product is well prevented, and the shelf-life is satisfactory.

EXAMPLE B-4

Hard Candy

Seventy hundred parts by weight of a syrupy saccharide composition containing maltohexaose and maltoheptaose, obtained by the method in Example A-3, was mixed with 90 parts by weight of sucrose, and the resultant mixture was concentrated by heating in vacuo until the moisture content lowered to below 2%. The concentrated solution was admixed with 0.15 parts by weight of citric acid and adequate amounts of a lemon flavor and a coloring agent, and the resultant mixture was formed in usual manner to obtain the desired product. The product is a high-quality hard candy having a satisfactory taste and biting property, as well as having a relatively-low hygroscopicity and a less stickiness.

EXAMPLE B-5

Radish Pickled in Sake Lees ("Bettara-Zuke")

Thirty kg of radish was in usual manner successively pickled with salt, saccharide, and 4 kg of a well-mixed composition consisting of one part by weight of a syrupy saccharide composition containing maltohexaose and maltoheptaose, obtained by the method in Example A-2, 3 parts by weight of maltose, 0.05 parts by weight of a powdered licorice, 0.008 parts by weight of malic acid, 0.07 parts by weight of sodium glutamate, 0.03 parts by weight of potassium sorbate and 0.2 parts by weight of pullulan. The product exerted a satisfiable gloss and texture, and had a satisfactory sweetness and biting property.

EXAMPLE B-6

Intubation Nutrition

A composition was prepared by mixing 20 parts by weight of a powdery saccharide composition containing maltohexaose and maltoheptaose, obtained by the method in Example A-4, 1.1 parts by weight of glycine, one part by weight of sodium glutamate, 0.4 parts by weight of calcium lactate, 0.1 part by weight of magnesium carbonate, 0.01 part by weight of thiamine, and 0.01 part by weight of riboflavin. Twenty-four g aliquots of the composition were distributed to laminated-aluminum small bags which were then heat sealed to obtain the captioned product. In use, one bag of the product is dissolved in about 33–500 ml water, and administered to the nasal cavity or stomach by the intubation feeding as an intubation nutrition. The product can be administered to not only human but also livestock.

EXAMPLE B-7

Intubation Nutrition

A composition was prepared by mixing 80 parts by weight of a powdery saccharide composition containing maltohexaose and maltoheptaose, obtained by the method in Example A-6, 190 parts by weight of dried yolk, 209 parts by weight of skim milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 parts by weight of vitamin E acetate and 0.04 parts by weight of nicotinamide. Twenty-five g aliquots of the composition were distributed to laminated-aluminum small bags which were then heat sealed to obtain the captioned product. In use, one bag of the product is dissolved in about 150–300 ml water, and administered as an intubation nutrition to the nasal cavity, gullet and stomach by the intubation feeding.

EXAMPLE B-8

Tablet

Four parts by weight of a powdery saccharide composition containing maltohexaose and maltoheptaose, obtained by the method in Example A-6, was mixed to homogeneity with 50 parts by weight of aspirin, 10 parts by weight of maltose and 4 parts by weight of corn starch, and the resultant mixture was tabletted by a 20 R punch having a diameter of 12 mm to obtain a tablet, 680 mg in weight, 5.25 mm in thickness and 8±1 kg in hardness. The product is a readily-swallowable tablet with an adequate sweetness.

EXAMPLE B-9

Milky Lotion

A half part by weight of polyoxyethylene behenyl ether, one part by weight of polyoxyethylene sorbitol tetraoleate, one part by weight of oil-soluble glyceryl monostearate, 0.5 parts by weight of behenyl alcohol, one part by weight of avocado oil, 3.5 parts by weight of a syrupy saccharide composition rich in maltohexaitol, obtained by the method in Example A-9, one part by weight of α-glycosyl rutin and appropriate amounts of vitamin E and antiseptic were mixed by heating in usual manner, and the mixture was mixed with 5 parts by weight of 1,3-butyleneglycol, 0.1 part by weight of carboxyvinyl polymer and 85.3 parts by weight of refined water. The mixture thus obtained was emulsified by a homogenizer. The product is a moisture-retaining milky lotion which is favorably usable as a sunscreen agent or a skin-whitening agent.

EXAMPLE B-10

Skin Cream

Two parts by weight of polyoxyethylene glycol monostearate, 5 parts by weight of self-emulsifying glyceryl monostearate, 2 parts by weight of α-glycosyl rutin, one part by weight of liquid paraffin, 10 parts by weight of glyceryl trioctanate, 4 parts by weight of a powdery saccharide composition containing maltohexaose and an adequate amount of an antiseptic were dissolved by heating, and the resultant solution was mixed with 5 parts by weight of 1,3-butylene glycol and 66 parts by weight of refined water. The resultant mixture was emulsified by a homogenizer and admixed with an adequate amount of a flavor while stirring to obtain a skin cream. The product is a cream with a satisfactory spreadability and suitably usable as a sunscreen cream, a skin-refining agent or a skin-whitening agent.

EXAMPLE B-11

Dentifrice

Forty-five parts by weight of calcium hydrogen phosphate, 1.5 parts by weight of sodium laurate, 25 parts by weight of glycerine, 0.5 parts by weight of polyoxyethylene sorbitan laurate, 15 parts by weight of a syrupy saccharide composition rich in maltohexaose and maltoheptaose, obtained by the method in Example A-5, 0.02 parts by weight of saccharin and 0.05 parts by weight of antiseptic were mixed with 13 parts by weight of water. The product with a superior gloss and detergency is suitably used as a dentifrice.

EXAMPLE B-12

Fertilizer in the Form of Rod

Seventy parts by weight of a compound fertilizer comprising 14% N, 8% $P_2O_5$, 12% $K_2O$, 5 parts by weight of pullulan, 5 parts by weight of a saccharide composition containing maltohexaose and maltoheptaose, obtained by the method in Example A-3, 15 parts by weight of calcium sulfate and 5 parts by weight of water were mixed to homogeneity, and the resultant mixture was heated to 80° C. by an extruder under the conditions of an L/D ratio of 20, a pressure ratio of 1.8 and a die diameter of 30 mm, to obtain the captioned product. In use, the product does not require a special vessel for carrying, and has a readily handleability and a satisfactory strength for a total layer application. The elution speed of the ingredients contained in the product is controllable by varying the composition. If necessary, the product can be readily admixed with one or more plant hormones, agricultural chemicals and soil conditioners.

As is described above, the present inventors found that the present AMYLASE has a relatively-high optimum temperature and thermal stability, as well as a relatively-wide range of optimum pH and stable pH. Furthermore, they found that the yield of the present AMYLASE produced by microorganisms is considerably high, and this renders it readily be used in the production of saccharide compositions rich in maltohexaose and/or maltoheptaose and those rich in maltohexaitol and/or maltoheptaitol from amylaceous substances. Thus, the present invention has a great significance in this field.

In addition, the saccharide compositions rich in maltohexaose and/or maltoheptaose and their hydrogenated products can be used as a sweetener with less sweetness in a variety of compositions, for example, a body-imparting agent, viscosity-controlling agent, moisture-retaining agent, and gloss-imparting agent, and also used as a nutrition-supplementing agent in a variety of compositions such as foods, beverages, cosmetics, pharmaceuticals and shaped products.

We claim:

1. A process for producing a maltohexaose and maltoheptaose-forming amylase which has an activity of mainly forming maltohexaose and maltoheptaose from starch, but does not substantially have an activity of hydrolyzing maltoheptaose and a lower molecular oligosaccharide than maltohexaose, which process comprises culturing in a nutrient culture medium a microorganism selected from the group consisting of strains of the species *Alcaligenes latus* and their mutants capable of forming said amylase, and recovering the formed amylase from the culture.

2. The process as claimed in claim 1, wherein said microorganism is *Alcaligenes latus* D2271 (FERM BP-4578).

3. The process as claimed in claim 1, wherein said nutrient culture medium contains not higher than 20 w/w % of starch on a dry solids basis, and the culture is effected at a temperature of 10–40 C., a pH of 5–8 and a dissolved oxygen concentration of 0.5–20 ppm for 10–100 hours.

* * * * *